United States Patent [19]

Danielson et al.

[11] Patent Number: 5,162,219
[45] Date of Patent: Nov. 10, 1992

[54] PREPARATION OF AMINE-ENRICHED PROTEINS HAVING AN INCREASED ISOELECTRIC POINT

[75] Inventors: Susan J. Danielson; Donald P. Specht, both of Rochester, N.Y.

[73] Assignee: Eastman Kodak Company, Rochester, N.Y.

[21] Appl. No.: 540,428

[22] Filed: Jun. 18, 1990

[51] Int. Cl.$^5$ .................... C12N 9/08; C12P 13/00
[52] U.S. Cl. .................................. 435/192; 435/128
[58] Field of Search .................... 435/192, 128, 132

[56] References Cited

U.S. PATENT DOCUMENTS

| | | | |
|---|---|---|---|
| 3,947,324 | 3/1976 | Lakshminarayanan | 435/192 |
| 4,089,747 | 5/1978 | Bruschi | 435/10 |
| 4,256,833 | 3/1981 | Ali et al. | 435/192 |
| 4,877,724 | 10/1989 | Chen et al. | 530/354 |

FOREIGN PATENT DOCUMENTS 2731921  1/1978  Fed. Rep. of Germany .

OTHER PUBLICATIONS

Hoare et al., J. of Biol. Chem., vol. 242, No. 10, pp. 2447-2453, 1967.
Zeffren et al., *The Study of Enzyme Mechanisms*, pp. 35-48 & 52, 1973.
Shannon et al., *Peroxidase Isozymes from Horseradish Roots*, J. of Biol. Chem., vol. 241, No. 9, pp. 2166-2172, 1966.
Aibara et al., *Isolation and Properties of Basic* . . . , J. Biochem., 90, pp. 489-496, 1984.
Aibara et al., *Isolation and Characterization of Five* . . . , J. Biochem. 92, pp. 531-539, 1982.

*Primary Examiner*—David M. Naff
*Assistant Examiner*—Mike Meller
*Attorney, Agent, or Firm*—John R. Everett

[57] ABSTRACT

Amine-enriched proteins, having an increased isoelectric point are provided by reacting a naturally occurring protein with an amide bond forming agent in the presence of a polyamine or a salt thereof. Such amine-enriched proteins such as enzymes are useful as labels in immunoassays.

5 Claims, No Drawings

PREPARATION OF AMINE-ENRICHED PROTEINS HAVING AN INCREASED ISOELECTRIC POINT

FIELD OF THE INVENTION

The present invention relates to amine-enriched proteins such as horseradish peroxidase, and methods for its preparation and use in immunoassays.

BACKGROUND OF THE INVENTION

Immunoassays, which take advantage of natural immunological reactions, have found widespread use as analytical techniques in clinical chemistry. Because of the specificity of the reactions, they are particularly advantageous in quantifying biological analytes (called ligands herein) including, for example, antibodies, therapeutic drugs, narcotics, enzymes, hormones, proteins, etc.

In competitive binding assays, a labeled ligand analog (sometimes referred to as ligand analog herein) is placed in competition with the unlabeled ligand for reaction with a fixed amount of the appropriate binding material (called a receptor herein). Unknown concentrations of the ligand can be determined from the measured signal of either the bound or unbound (i.e. free) ligand analog. The reaction proceeds as follows:

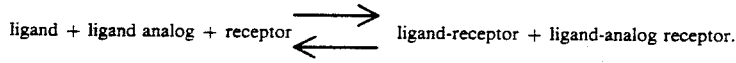

ligand + ligand analog + receptor ⇌ ligand-receptor + ligand-analog receptor.

Useful labels include proteins such as the peroxidases, including horseradish peroxidase (HRP). HRP, for example, has many properties which make it a desirable enzyme for use in enzyme immunoassays including its detectability at low concentrations, a pH optimum compatible with good antigen-antibody binding, long-term stability, low cost and absence of endogenous activity in patient samples.

Many methods for coupling ligands to proteins require the availability of reactive amino groups on the protein. The problem is that proteins such as naturally occurring HRP contain very few reactive amine groups. The number reported varies between 0 and 7 depending on the method of purification used. Thus the methods for coupling enzymes such as HRP to ligands through amine groups results in a significant fraction of unreacted enzyme.

SUMMARY OF THE INVENTION

The present invention provides amine-enriched proteins such as enzymes, including peroxidases such as horseradish peroxidase (referred to sometimes herein as amine-enriched HRP).

The present invention also provides an amine-enriched horseradish peroxidase which allows the preparation of labeled ligands with greater immunoreactivity with receptors than naturally occurring horseradish peroxidase.

The present invention also provides a method of making amine-enriched protein comprising the step of reacting a naturally occurring protein with an amide forming agent in the presence of a polyamine or a salt thereof.

The present invention also provides an immunoassay for ligand comprising the steps of:

a) providing an amine enriched enzyme labeled ligand wherein the amine enriched enzyme labeled ligand;

b) mixing a solution containing a ligand with a);

c) reacting the mixture from b) with a known amount of an antibody for the ligand wherein the antibody is bound to a solid matrix;

d) removing the unbound ligand and the amine enriched enzyme labeled ligand by washing the matrix; and e) measuring the amount of the labeled ligand by determining the amount of amine-enriched enzyme bound to the solid matrix.

DETAILS OF THE INVENTION

We have found that the reaction of HRP with a amide bond forming reagent in the presence of polyamines results in the conversion of some of the free carboxyl groups of the HRP into the monoamides of the polyamines, thereby introducing additional amino groups into the HRP.

Useful polyamines have two or more amine groups and include ethylenediamine, N-methylethylene diamine, N,N'-dimethylethylenediamine, diethylene triamine, piperazine, N-(2-aminoethyl)piperazine, hexanediamine lysine, lysyllysine, spermidine, and peptides containing at least two amines. Preferably the amines are added to the reaction mixture as a salt; more preferably as a hydrohalide salt derived from HCl or HBr. Thus, for example, ethylenediamine can be added to the reaction as the dihydrochloride HCl·NH$_2$—CH$_2$—CH$_2$NH$_2$·HCl.

The amide forming agent for use in this invention can include, for example, carbodiimides as reported in Erich Schmidt, Fritz Hitzles, Eberhard Lahde, *Berichte der Deutschen Chemischen Gesellshaft*, Vol. 71 II, p. 1933 (1938) and *Bull. Soc. Chem. France*, p. 1360 (1956); dihydroquinone compounds as described in German Patent Application (OLS) No. 2,322,317; carbamoylpyridinium compounds as described in German Patent Application (OLS) Nos. 2,225,230, 2,317,677 and 2,439,551; carbamoyloxypyridinium compounds as described in German Patent Application (OLS) No. 2,408,814); and dication ethers as described in U.S. Pat. No. 4,877,724.

Such compounds are described and illustrated in U.S. Pat. No. 4,863,841; see especially column 11, line 63, to column 21, line 42. The description pertaining to such materials in U.S. Pat. No. 4,863,841, supra, is incorporated by reference herein as if fully set forth. Of these agents, certain are preferred. A class of preferred amide forming agents has the formula:

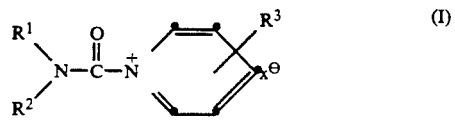

(I)

wherein R$^1$ and R$^2$ (which may be the same or different) each represents an alkyl group having from 1 to 10 carbon atoms (e.g., a methyl group, an ethyl group, a 2-ethylhexyl group, etc.) an aryl group having from 6 to 15 carbon atoms (e.g. a phenyl group, a naphthyl group, etc.), or an aralkyl group having from 7 to 15 carbon atoms (e.g., a benzyl group, a phenethyl group, etc.). Also, it is preferred that said $R^1$ and $R^2$ combine with each other to form a heterocyclic ring together with a nitrogen atom. Examples of forming a ring are a pyrrolidine ring, a piperazine ring, a morpholine ring, etc.

$R^3$ in formula (I) represents a substituent such as a hydrogen atom, a halogen atom, a carbamoyl group, a sulfo group, a ureido group, an alkoxy group having from 1 to 10 carbon atoms, an alkyl group having from 1 to 10 carbon atoms, etc. When $R^3$ is an alkoxy group or an alkyl group, these groups may be substituted by a substituent such as a halogen atom, a carbamoyl group, a sulfo group, or a ureido group.

$X^\ominus$ in formula (I) represents an anion and becomes a counter ion for the N-carbamoylpyridinium cation. When the amide forming agent of formula (I) forms an intramolecular salt, said $x^\ominus$ is not necessary. Examples of the anion represented by $x^\ominus$ are a halide ion, a sulfate ion, a sulfonate ion, $ClO_4^\ominus$, $BF_4^\ominus$, $PF_6^\ominus$, etc.

Another class of amide forming agents which may be used has Formula (II) as follows,

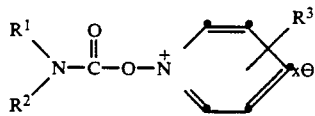

(II)

wherein $R^1$, $R^2$, $R_3$, and $x^\ominus$ have the same meanings as defined for Formula (I).

Another class of amide bond forming agents which can be used in this invention has the formula

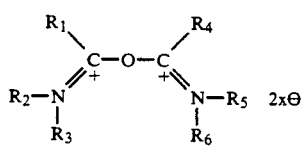

$R_1$ represents hydrogen, alkyl of 1 to 20 carbon atoms, aralkyl of 7 to 20 carbon atoms, aryl of 6 to 20 carbon atoms, $-YR_7$, the group

or the group

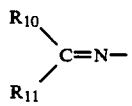

wherein Y represents sulfur or oxygen, and $R_7$, $R_8$, $R_9$, $R_{10}$, and $R_{11}$ each independently represents alkyl of 1 to 20 carbon atoms, aralkyl of 7 to 20 carbon atoms, aryl of 6 to 20 carbons atoms, or alkenyl of 2 to 20 carbon atoms or $R_8$ and $R_9$ together form a heterocyclic ring, or $R_{10}$ and $R_{11}$ are each independently hydrogen or together form a ring structure, or $R_1$ together with $R_2$ or $R_3$ forms a heterocyclic ring, $R_2$ and $R_3$ each independently represents alkyl of 1 to 20 carbon atoms, aralkyl of 7 to 20 carbon atoms, aryl of 6 to 20 carbon atoms, or alkenyl of 2 to 20 carbon atoms, or, taken together with $R_1$ or each other, forms a heterocyclic ring, $R_4$, and $R_5$, and $R_6$ are defined as are $R_1$, $R_2$, and $R_3$ respectively and are the same as or different from $R_1$, $R_2$, or $R_3$, and $x^\ominus$ represents an anion or an anionic portion of the compound to form an intramolecular salt.

These compounds are described in U.S. Pat. No. 4,877,724, supra; the description thereof in that patent is incorporated by reference herein as if fully set forth.

Examples of amide bond forming agents useful in this invention are:

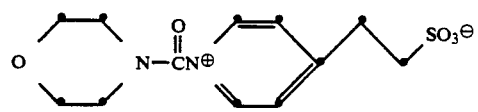

1-(4-Morpholinocarbonyl)-4-(2-sulfoethyl)-pyridinium hydroxide, inner salt (MSPH)

1-ethyl-3-(3-dimethylaminopropyl)carbodiimide hydrochloride (EDC)

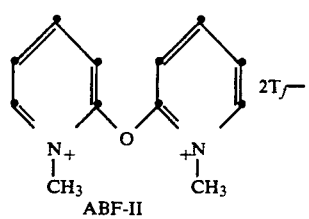

ABF-II

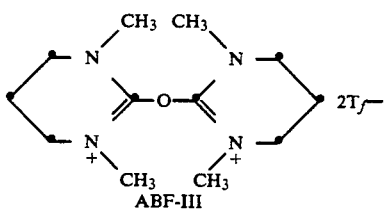

ABF-III

In the above formula $T_f$ stands for "triflate"; i.e. the trifluoromethanesulfonate anion, $CF_3SO_2O^-$.

Generally the reaction of (a) proteins such as HRP, (b) the polyamine (or salt thereof), and (c) amide forming agent is conducted in an aqueous reaction medium preferably containing about 0.5 to 50 mg/ml protein, and amide forming agent in an amount equivalent to 10 to 1000 fold excess over the moles of HRP (or from about 0.1 to 10 times the number of free carboxy groups in the aspartic and glutamic acid moieties in the HRP), and the polyamine in an amount equivalent to 1.5 to 10 times the amount of moles of amide forming reagent. The reaction is preferably conducted at temperatures between 4° and 40° C. for 15 minutes to 24 hours. The reaction should be conducted in an appropriate buffer at a pH of 4-7. After the amine-enriched HRP is formed, it is dialyzed or filtered thoroughly to remove excess amine and amide bond-forming reagent. If desired, the amine-enriched HRP can be exchanged into any of a number of suitable buffers for long-term storage or for subsequent reactions. A preservative can be added to prevent degradation by biological organisms.

For example the method of the invention for making amine-enriched HRP is carried out by dissolving the HRP in a buffer such as 2-(N-morpholino)ethanesulfonic acid (MES) at a concentration between 2 and 20 mg/ml at a pH between 5 and 6.5. The HRP solution is then combined with a solution of the amine (generally about 100 to 1000 fold excess over the moles of HRP) in the same buffer at the same pH. Equal volumes of the two solutions can be combined.

A freshly prepared solution of amide bond forming agent dissolved in a small amount of the same buffer is added to the above solution (generally about 20 to 500 fold excess over the moles of HRP).

The reaction is stirred or mixed by end-over-end rotation for about 1 hour to 24 hours.

Following the reaction excess amine and amide bond forming agents are removed by extensive dialysis against an appropriate buffer. For example, for long term storage stability of the HRP 3-(N-morpholino)propanesulfonic acid is preferred. Merthiolate or other appropriate preservatives can be added.

Amine-enriched HRP prepared according to the above described method contain no aggregates detectable by either reducing or nonreducing SDS-PAGE gels. This means that the method of the invention does not lead to formation of crosslinked HRP which could be caused by the amines on native HRP or amine-enriched product forming a covalent bond with the carboxyl groups of another HRP molecule. RZ (Reinheitzahl) is the absorbance ratio $A_{403}/A_{280}$. This value is an expression of the ratio of Hemin to Protein content. Procedures which lead to loss of hemin will result in a lower RZ ratio. The $A_{403}/A_{280}$ ratios of the products remain high at 3/1 and thus are unchanged from the native HRP. This means that the method of the invention does not lead to the loss of heme from the HRP. The retention of HRP activity following derivatization remains high at >85% retention of activity. This means that the method of the invention does not lead to inactivation or loss of HRP enzymatic activity.

The amine-enriched proteins of this invention were characterized by isoelectric focusing (IEF). The technique of isoelectric focusing is carried out electrophoretically in a pH gradient. In this technique proteins migrate until they; align themselves at their isoelectric point, pI. This method of protein characterization is well known. The method was carried out on commerically available LKB Ampholine PAG plates following the manfacturer's instructions. The plates used had a pH range of 3.5 to 9.5 (catalog No.1804-101).

The isoelectric point for proteins subjected to the above described method of the invention was always greater than the naturally occurring protein. For example the pI of the naturally occurring HRP used in these tests was about 9. The pI of amine-enriched HRP resulting from the method of the invention was always greater than 9, usually greater than or equal to 9.5. It will be understood by those skilled in the art that naturally occurring proteins such as HRP obtained from different sources or other proteins will have different pI's. Nevertheless the amine-enriched version will always have a greater pI.

The amine-enriched enzyme labeled ligand are useful in dry analytical elements designed to carry out immunoassays. Such elements typically comprise a support layer, a reagent zone, and a spreading zone. The two zones can be combined into a single layer or can be separate layers. Exemplary layer formats are:

A. 1) Bead spreading zone with immunoreagent(s) (antibodies)
2) Gelatin or polymer zone with reagents (buffer, amine-enriched HRP labeled ligand, etc.)
3) Support B. 1) Bead spreading zone
2) Bead—immunoreagent zone
3) Gelatin or polymer reagent zone
4) Support C. 1) Bead spreading zone
2) Bead layer with bound immunoreagent
3) Gelatin or polymer enzyme conjugate zone (water soluble)
4) Gelatin reagent zone
5) Support Format C. is disclosed in U.S. application Ser. No. 444,079 filed Nov. 30, 1989 entitled "Dry Immunoassay Analytical Element Comprising Monodispersed Beads" by L. A. Mauck et al, which employ monodisperse polymer beads of two different sizes coated either in separate layers or in a mixture in a single layer.

In certain assays in which amine enriched-enzymes such as HRP are useful, one or more reagents are added to the ligand sample to be analyzed rather than being included in the analytical element. For example, in a digoxin assay, amine-enriched HRP labeled digoxin is mixed with the sample. The mixture is spotted on an element having a mixture of large and small beads in accordance with the aforementioned patent application of Mauck et al, and as specified on page 8 of U.S. application Ser. No. 444,079. Generally, the element comprises: a support, a gelating layer with certain reagents coated on the support, and a spreading-reagent layer coated on the gelatin layer as follows:

ELEMENT STRUCTURE FOR DIGOXIN

|  | Coverage (g/m²) Preferred |
|---|---|
| Spreading Layer: | |
| Large Beads, 30 μm | 130 |
| Small Beads with Antibodies (0.5 μm-2.5μ) | 0.001-0.1* |
| Triarylimidazole Leuco Dye | 0.2 |
| Dimethyl sulfoxide | 2 |
| Binder | 3 |
| 3-(N-morpholino)propane sulfonic acid MOPS Buffer, pH 7.0 | 0.2 |
| Kelzan TM (Kanthan gum from Kelco | 0.07 |
| 5,5-Dimethyl-1,3-cyclohexanedione | 0.05 |
| surfactant Zonyl FSN (duPont) | 0.05 |
| Gelatin Layer: | |
| Hardened Gelatin | 10 |
| 4'-Hydroxyacetanilide | 0.2 |
| Potassium Phosphate Buffer, pH 7.0 | 0.5 |
| Surfactant Triton TX-100 (Rohm & Haas) | 0.02 |

*Depends on grams of antibody/grams of beads, which varies with antibody, beads and preparation.

After spotting the sample, the unknown digoxin and amine-enriched HRP labeled digoxin compete for complexation and immobilization on the small beads. The element is then treated with a wash solution and the uncomplexed digoxin and amine-enriched HRP labeled digoxin migrate to the edges of the wash solution. The digoxin and the labeled digoxin that are immobilized on the beads remain in the center of the element. The amine-enriched HRP label catalyzes dye formation from the leuco dye and the electron transfer agent, 4'-hydroxyacetanilide which migrates from the gelatin layer after wetting by the sample and wash solution. The density of the dye formed is then read, preferably at the center of the element where the labeled digoxin is immobilized. However the density could also be read elsewhere on the radius formed by the wash solution. The latter type of read-out may require migration of the unbound reagent to a remote mordanting or immobilization area (ring).

The element can comprise one or more layers, e.g. separate or combined reagent/spreading layer and a gelatin buffer layer containing other necessary additives, coupling enzymes, etc. The beads, can include both large and small polymeric beads, and they can either be coated in the same or different layers. The small beads can be coated before, concurrently with or after the large beads.

The reagent layer or the spreading layer of the element can contain the indicator composition comprising one or more reagents dispersed in one or more synthetic or natural binder materials, such as gelatin, or other naturally-occurring colloids, homopolymers and copolymers, such as poly(acrylamide), poly(vinyl pyrrolidone), poly(N-isopropylacrylamide), poly(acrylamide-co-N-vinyl-2-pyrrolidone) and similar copolymers.

Other optional layers, e.g. subbing layers, radiation-blocking layers, etc. can be included if desired. All layers of the element are in fluid contact with each other, meaning that fluids and reagents and uncomplexed reaction products in the fluids can pass between superposed regions of adjacent layers.

Additional layers can also be used, such as subbing layers, interlayers, etc. These layers can also contain reagents for the assays, if desired.

The substrate for the enzyme is present in the element or added thereto in the wash liquid. The substrate can be added to the element prior to or simultaneously with the liquid sample, or after completion of the binding reaction. It is within the skill of the ordinary worker in clinical chemistry to determine a suitable substrate for a given label. The substrate can be a material which is directly acted upon by the enzyme label, or a material that is involved in a series of reactions which involve enzymatic reaction of the label as is well known in this art. Those skilled in the art will know how to adjust the amount of a particular substrate for the amount of enzyme label used in the assay.

The reagent layer contains an indicator composition comprising one or more reagents which provide a detectable species as a result of reaction of the label. Preferably, the indicator composition is a colorimetric indicator composition which provides a colorimetrically detectable species as a result of the enzymatic reaction of amine-enriched HRP labeled ligand with the substrate.

The indicator composition can be a single compound which produces a detectable dye upon enzymatic reaction, or a combination of reagents which produce the dye. For example the composition can include a leuco dye and amine-enriched HRP. Useful leuco dyes are known in the art and include those, for example, described in U.S. Pat. No. 4,089,747 (issued May 16, 1978 to Bruschi) and U.S. Ser. No. 612,509, filed May 21, 1984 by Babb et al. The particular amounts of the colorimetric indicator composition and its various components are within the skill of a worker in the art.

The layers of the element can contain a variety of other desirable but optional components, including surfactants, thickeners, buffers, hardeners, antioxidants, coupler solvents, and other materials known in the art. The amounts of these components are also within the skill of a worker in the art.

The immunoassay can be manual or automated. In general, the amount of analyte in a liquid sample is determined by taking the element from a supply roll, chip packet or other source and physically contacting a finite area of the spreading layer with a sample of the liquid, e.g. 1 to 100 $\mu l$. The finite area which is contacted is generally no more than about 100 mm$^2$.

If the enzyme labeled ligand is not incorporated in the element during manufacture, it can be mixed with the test sample simultaneously with or prior to contact with the element.

After sample application in either embodiment, the element is exposed to any conditioning, such as incubation, heating or the like, that may be desirable to quicken or otherwise facilitate obtaining the test result.

The amount of ligand is determined by passing the element through a suitable apparatus for detecting the complexed ligand analog directly or the detectable species formed as a result of enzymatic reaction of an enzyme label and a substrate. For example, the species can be detected with suitable radiometric, fluorometric or spectrophotometric apparatus using generally known procedures. In an enzymatic reaction, the resulting product is determined by measuring, for example, the reflection of transmission density or fluorescence in the center of the finite area which was contacted with the test sample. The area which is measured is generally from about 3 to about 5 mm in diameter for competing assays. The amount of analyte in the liquid sample is inversely proportional to the amount of label measured in the center of the finite area. As mentioned hereinbefore, in a preferred embodiment a separate wash step is required in order to separate complexed ligand from uncomplexed ligand (radial wash). Generally, label measurement is carried out after from about 5 to about 180 seconds after sample contact and spreading or application of the wash liquid.

The following examples will demonstrate the method for making amine-enriched HRP, its immunoreactivity and utility in immunoassays.

EXAMPLE 1

Amine-Enrichment of HRP Using Ethylenediamine and MSPH

A solution of HRP in 0.1M MES buffer, pH=5.5, was prepared by dissolving 200 mg of HRP in 10 mL of the buffer (MES=2-(N-morpholino)ethanesulfonic acid). The protein concentration was determined by $A_{403}$ measurement ($A_{403}$/mg/mL=2.24) to be 15.1 mg/mL. The HRP (25 mg, 1.656 mL) was combined with 0.344 mL MES buffer and 50 mg of ethylendiamine dihydrochloride in a 15 mL conical polypropylene centrifuge tube. Amide bond forming agent 1-(4-morpholinocarbonyl)-4-(2-sulfoethyl)-pyridinium hydroxide, inner salt (500 $\mu L$ of a freshly prepared 75 mg/mL solution in MES buffer) was added, and the reaction was rotated end over end at room temperature for 6 hours. The reactions were dialyzed against 0.02M MOPS buffer, pH=7.0 (3 L at 10° C.)(MOPS=3-(N- morpholino)propanesulfonic acid). The dialysis buffer was changed twice. The results of an isoelectric focusing experiment indicated that there was no unreacted HRP remaining following reaction.

An amine-enriched HRP labeled digoxin activated hapten was found 100% immunoreactive when tested with digoxin antibody immobilized on beads. It performs well in an Ektachem radial wash immunoassay using the previously described Mauck et al element.

Amine-enriched HRP was also prepared by applying the method of this invention to the following combinations of polyamines and peptide bond forming agents.

EXAMPLE 2

Amine-Enrichment of HRP Using Spermidine and MSPH

EXAMPLE 3

Amine-Enrichment of HRP Using Spermidine and EDC

EXAMPLE 4

Amine-Enrichment of HRP Using Lysine and MSPH

EXAMPLE 5

Amine-Enrichment of HRP Using Lysine and EDC

EXAMPLE 6

Amine-Enrichment of HRP Using Lysyllysine and MSPH

EXAMPLE 7

Amine-Enrichment of HRP Using Lysyllysine and EDC

The invention has been described in detail with particular reference to preferred embodiments thereof, but it will be understood that variations and modifications can be effected within the spirit and scope of the invention.

We claim:

1. A method of making an amine-enriched protein having an isoelectric point greater than the isoelectric point of a naturally occurring protein used to produce the amine-enriched protein comprising the steps of reacting, in an aqueous medium, a naturally occurring protein with an amide bond forming agent in the presence of a polyamine or a salt thereof; wherein the amide forming agent is present in the amount equivalent to about 10 to 1,000 fold excess over the moles of protein and the polyamine is present in an amount equivalent to 1.5 to 10 times the amount of moles of the amide forming agent.

2. The method of claim 1 wherein the polyamine is selected from a class consisting of ethylenediamine, N-methylethylenediamine, N,N'-dimethylethylene diamine, diethylenetriamine, piperazine, N-(aminoethyl)-piperazine, hexanediamine, lysine, lysyllysine, spermidine and peptides containing at least two amines.

3. The method of claim 1 wherein the amide forming agent is selected from a class consisting of 1-(Morpholinocarbonyl)-4-(2-sulfoethyl)pyridinium hydroxide, inner salt (MSPH) and 1-ethyl-3-(3-dimethylaminopropyl) carbodiimide hydrochloride (EDC).

4. The amine-enriched protein made by the method of claim 1, 2 or 3.

5. An amine-enriched horseradish peroxidase made according to the method of claim 1, 2 or 3.

* * * * *